(12) United States Patent
Bigi et al.

(10) Patent No.: US 7,718,821 B1
(45) Date of Patent: May 18, 2010

(54) METHOD OF PREPARING ELECTRON DEFICIENT OLEFINS

(75) Inventors: Franca Bigi, Parma (IT); Stefano Gheradi, Pegognaga (IT); Ciaran B. McArdle, Dublin (IE)

(73) Assignees: Loctite (R&D) Limited, Dublin (IL); Universita Degli Studi di Parma, Parma (IT)

( * ) Notice: Subject to any disclaimer, the term of this patent is extended or adjusted under 35 U.S.C. 154(b) by 535 days.

(21) Appl. No.: 11/612,504

(22) Filed: Dec. 19, 2006

(51) Int. Cl.
 *C07C 255/23* (2006.01)
(52) U.S. Cl. ...................... 558/443; 564/271
(58) Field of Classification Search ................ 558/443; 564/271
See application file for complete search history.

(56) References Cited

U.S. PATENT DOCUMENTS

| | | | |
|---|---|---|---|
| 2,363,464 A | 11/1944 | Senkus | |
| 2,413,249 A | 12/1946 | Senkus | |
| 2,413,250 A | 12/1946 | Senkus | |
| 2,415,046 A | 1/1947 | Senkus | |
| 2,582,128 A | 1/1952 | Hurwitz | |
| 2,721,858 A | 10/1955 | Joyner at al. | |
| 2,756,251 A | 7/1956 | Joyner at al. | |
| 2,763,677 A | 9/1956 | Jeremias | |
| 3,142,698 A | 7/1964 | Halpern et al. | |
| 3,903,055 A | 9/1975 | Buck | |
| 3,975,422 A | 8/1976 | Buck | |
| 3,988,299 A | 10/1976 | Malofsky | |
| 4,003,942 A | 1/1977 | Buck | |
| 4,012,402 A | 3/1977 | Buck | |
| 4,013,703 A | 3/1977 | Buck | |
| 4,202,920 A | 5/1980 | Renner et al. | |
| 4,364,876 A | 12/1982 | Kimura et al. | |
| 4,512,357 A | 4/1985 | Earl | |
| 4,556,700 A | 12/1985 | Harris et al. | |
| 4,587,059 A | 5/1986 | Harth et al. | |
| 4,622,414 A | 11/1986 | McKervey | |
| 4,636,539 A | 1/1987 | Harris et al. | |
| 4,695,615 A | 9/1987 | Leonard et al. | |
| 4,718,966 A | 1/1988 | Harris et al. | |
| 4,837,260 A | 6/1989 | Sato et al. | |
| 4,855,461 A | 8/1989 | Harris | |
| 4,906,317 A | 3/1990 | Liu | |
| 5,142,098 A | 8/1992 | Bru-Magniez et al. | |
| 5,288,794 A | 2/1994 | Attarwala | |
| 5,306,752 A | 4/1994 | Attarwala | |
| 5,312,864 A | 5/1994 | Wenz et al. | |
| 5,328,944 A | 7/1994 | Attarwala et al. | |
| 5,424,343 A | 6/1995 | Attarwala | |
| 5,424,344 A | 6/1995 | Lewin | |
| 5,455,369 A | 10/1995 | Meier et al. | |
| 5,624,699 A | 4/1997 | Lang | |
| 5,703,267 A | 12/1997 | Takahashi et al. | |
| 5,744,642 A | 4/1998 | Lantzsch et al. | |
| 6,093,780 A | 7/2000 | Attarwala | |
| 6,096,848 A | 8/2000 | Gololobov et al. | |
| 6,245,933 B1 | 6/2001 | Malofsky et al. | |
| 6,291,544 B1 | 9/2001 | Kotzev | |
| 6,835,789 B1 | 12/2004 | Kneafsey et al. | |
| 2006/0094833 A1 | 5/2006 | McDonnell et al. | |

FOREIGN PATENT DOCUMENTS

| | | |
|---|---|---|
| EP | 0 459 617 A1 | 12/1991 |
| WO | WO 94/15590 A1 | 7/1994 |
| WO | WO 95/32183 | 11/1995 |
| WO | WO 99/14206 A1 | 3/1999 |
| WO | WO 03/006225 A1 | 1/2003 |
| WO | WO 03/086605 A2 | 10/2003 |

OTHER PUBLICATIONS

Carey & Sundberg, Advanced Organic Chemistry Part B: Reactions and Synthesis, 3rd Ed. Plenum Press, 1990, pp. 80-84.*
Danishefsky et al. J. Am. Chem. Soc. 1977, 99, 6066-6075.*
Gololobov et al. Russian Chemical Reviews 1997, 66(11), 953-962.*
Carl J. Buck, Unequivocal Synthesis of Bis(2-Cyanoacrylate) Monomers, I. Via Anthracene Adducts, *Journal of Polymer Science, Polymer Chemistry Edition*, vol. 16, 2475-507 (1978).
G. Jones, "The Knoevenagle Condensation", *Organic Reactions*, vol. XV, 204, Wiley New York (1967).
F. Bigi et al., "Montmorillonite KSF as an Inorganic, Water Stable, and Reusable Catalyst for the Knoevenagel Synthesis of Coumarin-3-carboxylic Acids", *Journal Organic Chemistry*, vol. 64, 1033-35 (1999).
B. Green et al., "Synthesis of Steroidal 16, 17-Fused Unsaturated 8-Lactones", *Journal Organic Chemistry*, vol. 50, 640-44 (1985).
P. Rao et al., "Zinc Chloride As A New Catalyst for Knoevenagel Condensation", *Tetrahedron Letters*, vol. 32, No. 41, 5821-22 (1991).

(Continued)

*Primary Examiner*—Rebecca L Anderson
*Assistant Examiner*—Jason M Nolan
(74) *Attorney, Agent, or Firm*—Steven C. Bauman

(57) ABSTRACT

This invention relates to a process for producing electron deficient olefins, such as 2-cyanoacrylates, using an iminium salt.

18 Claims, 1 Drawing Sheet

OTHER PUBLICATIONS

J. S. Yadav et al., "Phosphane-Catalyzed Knoevenagel Condensation: A Facile Synthesis of Cyanoacrylates and α-Cyanonitriles", *European Journal Organic Chemistry*, 546-51 (2004).

L. Tietze et al., Comprehensive Organic Synthesis, Pergamon Press, Oxford, vol. 2, Chapter 1.11, 341 (1991).

P. Laszlo, "Catalysis of Organic Reactions by Inorganic Solids", *Accounts of Chemical Research*, vol. 19, 121-27 (1986).

K. Kloestra et al., "Base and Acid Catalysis by the Alkali-containing MCM-41 Mesoporous Molecul Sieve", *Journal Chemical Soc. Chem. Commun.*, 1005-06 (1995).

P. Lednor et al., "The Use of a High Surface Area Silicon Oxynitride as a Solid, Basic Catalyst", *Journal Chemical Society, Chem. Commun.*, 1625-26 (1991).

F. Bigi et al., "A Revision of the Biginelli Reaction Under Solid Acid Catalysis. Solvent-free Synthesis of Dihydropyrimidines Over Montmorillonite KSF", *Tetrahedron Letters*, vol. 40, 3465-68 (1999).

F. Bigi et al., "Clean synthesis in water: uncatalysed preparation of ylidenemalononitriles", *Green Chemistry*, vol. 2, 101-03 (2000).

R. Breslow, "Hydrophobic Effects on Simple Organic Reactions in Water", *Accounts of Chemical Research*, vol. 24, 159-64 (1991).

C. Li, "Organic Reactions in Aqueous Media—With a Focus on Carbon-Carbon Bond Formation", *Chemical Reviews*, vol. 93, 2023-35 (1993).

T. Welton, "Room Temperature Ionic Liquids. Solvents for Synthesis and Catalysis", *Chemical Reviews*, vol. 99, 2071-83 (1999).

D. Morrison et al., "Base-promoted reactions in ionic liquid solvents. The Knoevenagel and Robinson annulation reactions", *Tetrahedron Letters*, vol. 42, 6053-55 (2001).

Fraga-Dubreiul et al., "Grafted ionic liquid-phase-supported synthesis of small organic molecules", *Tetrahedron Letter*, vol. 42, 6097-6100 (2001).

M. Smietana et al., "Preparation of Silyl Enol Ethers Using (Bistrimethylsilyl)acetamide in Ionic Liquids", *Organic Letters*, vol. 3, No. 7, 1037-39 (2001).

Li et al., "n-Butyl Pyridinium Nitrate as a Reusable Ionic Liquid Medium for Knoevenagel Condensation", *Chinese Chemical Letters*, vol. 14, No. 5, 448-50 (2003).

J. Harjani at al., "Lewis acidic ionic liquids for the synthesis of electrophilic alkenes via the Knoevenagel condensation", *Tetrahedron Letters*, vol. 43, 1127-30 (2002).

Xu et al., "Knoevenagel condensation Reaction Catalyzed by Functionalized Ionic Liquid 1-(2-Hydroxyethyl)-3-methyl Imidazolium Chloride", *Chinese Journal of Organic Chemistry*, vol. 24(10), 1253-56 (2004).

Su et al., "Organic Reactions in Ionic Liquids: Knoevenagel Condensation Catalyzed by Ethylenediammonium Diacetate", *Synthesis 2003*, No. 4, 555-59 (2003).

Moehrle et al., "Aminomethylierung von 1,3-Diketonen", *Pharmazie*, vol. 40, 697-701 (1985).

J. March, "Reactions", *Advanced Organic Chemistry*, 3rd Edition, Wiley & Sons Inc., 417 (1985).

J. March, "Addition to Carbon-Hetero Multiple Bonds", *Advanced Organic Chemistry*, 3rd Edition, Wiley & Sons, 802-03 (1985).

M. B. Smith, *Organic Synthesis*, McGraw Hill International Chemistry Series, 1302 (1994).

Tehrani et al., "Product Class 8: Iminium Salts", *Science of Synthesis*, vol. 27, 313-48 (2004).

B. Hin et al., "Facile Synthesis of α-Substituted Acrylate Esters", *Journal of Organic Chemistry*, vol. 67, 7365-68 (2002).

Holy et al., "The Mannich Reaction-II Derivatization of Aldehydes and Ketones Using Dimethyl(methylene)ammonium Salts", *Tetrahedron Letters*, vol. 35, 613-19 (1979).

Bryson et al., "Preformed Mannich Salts: A Facile Preparation of Dimethyl(methylene)ammonium Iodide", *Journal of Organic Chemistry*, vol. 45, 524-25 (1980).

J. March, "The Pinacol Rearrangement", *Advanced Organic Chemistry*, 3rd Edition, Wiley & Sons, 963-64 (1985).

J. March, "Free-Radical Substitution", *Advanced Organic Chemistry*, 3rd Edition, Wiley & Sons, 642 (1985).

Jahn et al., "A Novel and Simple Method for the Preparation of Iminium Salts", *Tetrahedron Letters*, vol. 34, No. 37, 5863-66 (1993).

R. J. Vijin et al., Synthesis, 573 (1994).

Davis, "Chemistry Letters", vol. 33, Issue 9, 1072-77 (2004).

Davis et al., "Ionic Liquids in Synthesis", P. Wasserscheid and T. Welton, eds., Wiley-VCH Verlag GmbH & Co. KGaA, Chapter 2 (2002).

M.G. Djamali, P. Burba, K.H. Lieser, "Snythese and Eigenschaften eines Celluloseaustauschers mit Diaminodibenzo-18-Krone-6 als Ankergruppe", *Die Angewandte Makromolecular Chemie*, vol. 92, 145-54 (1980).

K. Babic, "Reactive and Functional Polymers", vol. 66, 1494-1505 (2006).

Trumbo et al., "Copolymerization Behavior of 3-Isopropenyl-α,α-Dimethylbenzylamine and Preliminary Evaluation of the Copolymers in Thermoset Coatings", *Journal of Applied Polymer Science*, vol. 82, 1030-39 (2001).

T. Giesenberg et al, "Synthesis and Functionalization of a New Kind of Silica Particle." *Agnew. Chem. Int. Ed.*, 43, 5697-5700 (2004).

Zhang et al., "An Investigation of Knoevenagel condensation reaction in microreactors using a new zeolite catalyst", *Applied Catalysis A: General*, 261, 109-118 (2004).

Mehnert et al., "Chemical Communications", 3010 (2002).

Lee and Lee, "Bulletin of the Korean Chemical Society", vol. 25, Issue 10, 1531-37 (2004).

H. R. Snyder and W. E. Hamlin, "Alkylation of Nitroparaffins with Amines and Their Derivatives", *Journal of American Chemical Society*, vol. 72, 5082-85 (1950).

H. G. Johnson, "Reaction of Aliphatic Amines with Formaldehyde and Nitroparaffins. II. Secondary Amines", *Journal of American Chemical Society*, vol. 68, 12-14 (1946).

M. Semkus, "Journal of the American Chemical Society", vol. 68, 10-12 (1946).

Sarac, "Progress in Polymer Science", vol. 24, 1149-1201 (1999).

Brough et al., "Pyrimidinyl Nitronyl Nitroxides", *Chemical European Journal*, vol. 12, 5134 (2006).

Zhou et al., *J. Polym. Sci., Part A Polym. Chem. Ed.*, 29, 1097 (1991).

Mehrotra et al., "Journal of Organometalic Chemistry", vol. 24, 611-21 (1970).

Son et al., "Synthesis of Hexahydro-3,3,5,5,7-pentaalky1-2H-1,4-diazepin-2-ones from 1,3-Diamines and Ketones", *J. Org. Chem.*, vol. 46, 323 (1981).

Senkus, Acetals of Nitro Alcohols and Corresponding Amino Acetals, *J. Amer. Chem. Soc.*, vol. 69, 1380-81 (1947).

Renner et al., "Cure of Epoxy Resins with Esters of Cyanoacrylic Acid", *Journal of Polymer Science: Polymer Chemistry Edition*, vol. 23, 2341 (1985).

Kennedy et al., "Macromers by Carbocationic Polymerization. X. Synthesis, Characterization, and Polymerizability of Cyanoacrylate-Capped Polyisobutylenes", *Journal of Macromolecular Science*, Part A, 28:2, 209-24 (1991).

Khrustalev et al., "Synthesis and X-ray structural study of 1-adamantylmethy 2-cyanoacrylatel and 1,10-decanediol bis-2-cyanoacrylate", *Russian Chemical Bulletin*, vol. 45, No. 9, 2172 (1996).

Y. Gololobov et al., "A novel approach to the synthesis of bis(2-cyanoacrylates)", *Russian Chemical Bulletin*, vol. 42, No. 5, 961 (1993).

Y. Gololobov et al., "Synthesis of bis(2-cyanoacrylates) from 2-cyanoacryloyl chloride and 2-butene-and 2-butyne-1,4-diols", *Russian Chemical Bulletin*, vol. 44, No. 4, 760 (1995).

J.-L. De Keyser et al., "A Versatile and Convenient Multigram Synthesis of Methylidenemalonic Acid Diesters", *J. Org. Chem.*, vol. 53, 4859 (1988).

Vijayalakshmi at al., "Alkyl and substituted alkyl 2-cyanoacrylates. Part I. Synthesis and Properties", *J. Adhesion Science Technology*, vol. 4, No. 9, 733 (1990).

Guseva et al., "Organic Chemistry. Synthesis of functionality substituted cyanoacetates." *Russian Chemical Bulletin*, vol. 42, No. 3, 478 (1993).

Guseva et al., "Organic Chemistry" *Russian Chemical Bulletin*, vol. 43, No. 4, 595 (1995).

Gololobov and Gruber, Russian Chemical Review, vol. 66, Issue 11, 953 (1997).

Senchenya et al., "Silicon-containing esters of α-cyanoacrylic acid: synthesis and properties" *Russian Chemical Bulletin*, vol. 42, No. 5, 909 (1993).

Bowie J. H. et al., "Tetrahedron", vol. 23, 305-20 (1967).

J. S. Norwick at al., J. Org. Chem., 57(28), 7364-66 (1992).

* cited by examiner

Reactions A, B, and C respectively

METHOD OF PREPARING ELECTRON DEFICIENT OLEFINS

BACKGROUND OF THE INVENTION

1. Field of the Invention

This invention relates to a process for producing electron deficient olefins, such as 2-cyanoacrylates, using an iminium salt.

2. Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.*, 16, 2475-2507 (1978), and U.S. Pat. Nos. 3,975,422, 3,903,055, 4,003,942, 4,012,402, and 4,013,703]. A variety of other processes for producing cyanoacrylate monomers are known, and some of which are described below.

U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a polyethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel condensation reaction conditions, as noted above. Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect may also enable facile access to highly useful difunctional monomers, such as so-called bis-cyanoacrylates or hybrid materials of cyanoacrylate and other polymerisable or reactive functionality.

In H. Mohrle and R. Schaltenbrand, "Aminomethylierung von 1,3-Diketonen", *Pharmazie*, 40, 697-701 (1985), reference is made to dialkyl(methylene)iminium chloride salts. Such iminium chloride salts are not protonated, but rather alkylated. The products from the reaction with the so described dialkyl(methylene)iminium chloride salts are protonated Mannich bases.

Absent from the published literature is the use of protonated iminium salts (hereafter referred to as "iminium salt(s)") in the preparation of 2-cyanoacrylates. Until now.

SUMMARY OF THE INVENTION

Unlike the state of the technology, the present invention provides a direct or "crackless" synthesis of electron deficient olefins, specifically 2-cyanoacrylate monomers, using an iminium salt. The synthesis hereby provided may be catalysed or uncatalysed.

The present invention provides a process for the preparation of a reactive electron deficient olefin. In one aspect, the invention includes the steps of:

(a) providing an iminium salt and a compound containing a methylene linkage having at least one electron withdrawing substituent attached thereto, where the electron withdrawing substituent is selected from nitrile, carboxylic acids, carboxylic esters, sulphonic acids, ketones or nitro;

(b) reacting the iminium salt and the compound under appropriate conditions and for a time sufficient yield a reactive electron deficient olefin; and (c) optionally, separating from the mixture the so formed reactive electron deficient olefin to yield the reactive electron deficient olefin substantially free from the iminium salt, the compound and solvent.

In another aspect, the invention provides a process for the preparation of a reactive electron deficient olefin that includes the steps of:

(a) providing as reactants an aldehyde compound having the structure R—CH=O, where R is hydrogen or vinyl and a primary amine to form an imine;

(b) contacting the imine formed in step (a) with acid to form an iminium salt;

(c) providing a 2-electron withdrawing group-substituted methylene compound and reacting the iminium salt from step (b) therewith to form an electron deficient olefin; and (d) optionally, separating from step (c) the so formed reactive electron deficient olefin to yield the reactive electron deficient olefin substantially free from reactants and solvent.

In yet another aspect, the invention provides a process for the preparation of a 2-cyanoacrylate ester. The steps of this process include (a) providing as reactants an aldehyde compound (or a source of an aldehyde compound) having the structure R—CH═O where R is hydrogen, and a primary amine;

(b) reacting the mixture of reactants under appropriate conditions and for a time sufficient to yield an imine;

(c) contacting the imine formed in step (b) with acid to form an iminium salt;

(d) providing a cyanoacetate and reacting the iminium salt from step (c) therewith to form 2-cyanoacrylate ester; and (e) optionally, separating from the mixture the so-formed 2-cyanoacrylate ester to yield 2-cyanoacrylate ester substantially free from reactants and solvent.

In any of these aspects, the process may be conducted with or without added catalyst. When a catalyst is added, desirably the catalyst should be one that is not a solely basic nucleophile. Thus, an acidic system would be preferred and a ditropic system may be used, as well.

DETAILED DESCRIPTION OF THE INVENTION

Figure 1:
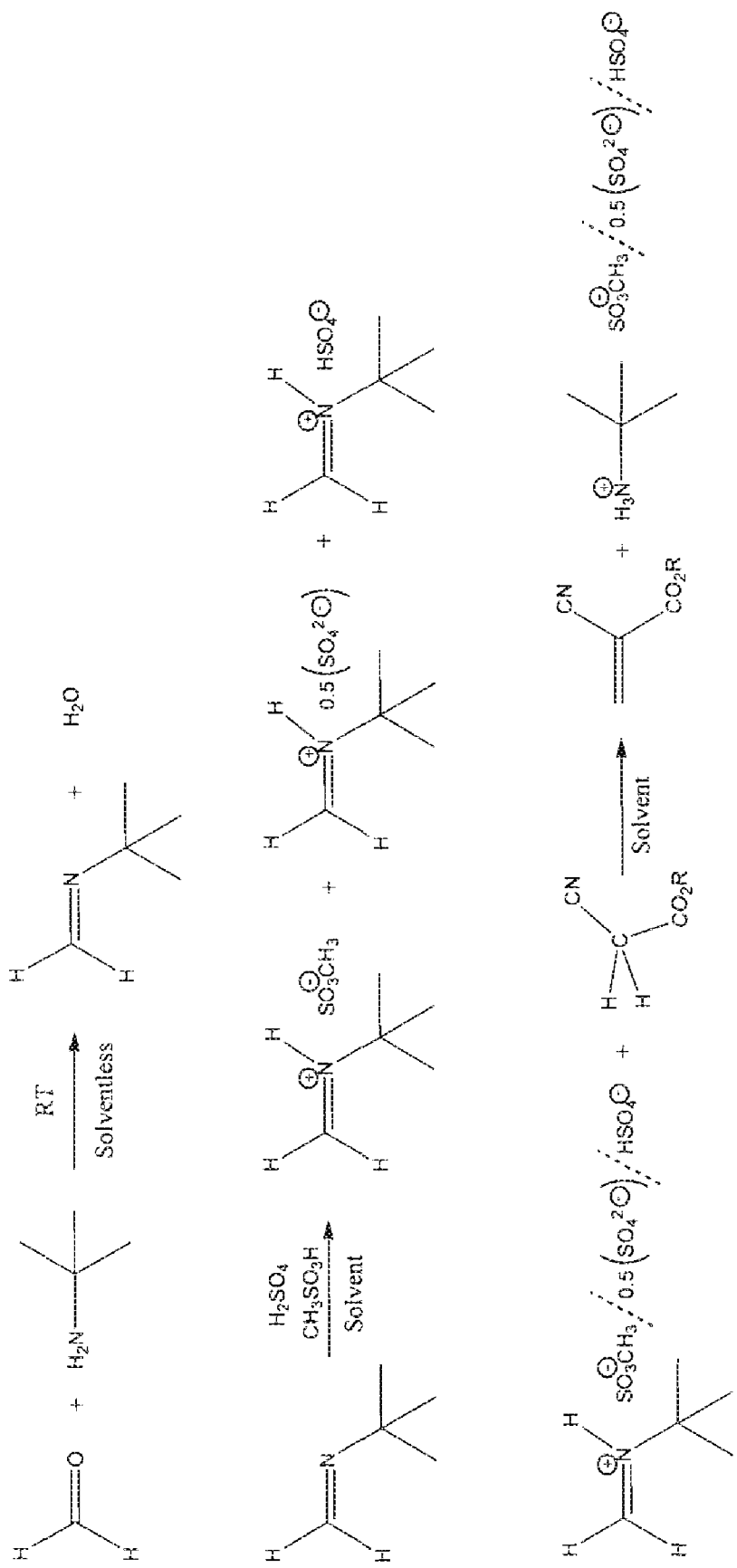
FIG. 1 depicts a synthetic scheme according to the present invention.

As noted above, the present invention provides a process for the preparation of a reactive electron deficient olefin. In one aspect, the invention includes the steps of:

(a) providing an iminium salt and a compound containing a methylene linkage having at least one electron withdrawing substituent attached thereto, where the electron withdrawing substituent is selected from nitrile, carboxylic acids, carboxylic esters, sulphonic acids, ketones or nitro;

(b) reacting the iminium salt and the compound under appropriate conditions and for a time sufficient to yield a reactive electron deficient olefin; and (c) optionally, separating from the mixture the so formed reactive electron deficient olefin to yield the reactive electron deficient olefin substantially free from the iminium salt, the compound and solvent.

In another aspect, the invention provides a process for the preparation of a reactive electron deficient olefin that includes the steps of:

(a) providing as reactants an aldehyde compound having the structure R—CH═O, where R is hydrogen or vinyl and a primary amine to form an imine;

(b) contacting the imine formed in step (a) with acid to form an iminium salt;

(c) providing a 2-electron withdrawing group-substituted methylene compound and reacting the iminium salt from step (b) therewith to form a reactive electron deficient olefin; and (d) optionally, separating from step (c) the so formed reactive electron deficient olefin to yield the reactive electron deficient olefin substantially free from reactants and solvent.

In yet another aspect, the invention provides a process for the preparation of a 2-cyanoacrylate ester. The steps of this process include (a) providing as reactants an aldehyde compound (or a source of an aldehyde compound) having the structure R—CH═O where R is hydrogen, and a primary amine;

(b) reacting the mixture of reactants under appropriate conditions and for a time sufficient to yield an imine;

(c) contacting the imine formed in step (b) with acid to form an iminium salt;

(d) providing a cyanoacetate and reacting the iminium salt from step (c) therewith to form 2-cyanoacrylate ester; and (e) optionally, separating from the mixture the so-formed 2-cyanoacrylate ester to yield 2-cyanoacrylate ester substantially free from reactants and solvent.

Of course, the invention also provides a process for using iminium salts to prepare reactive electron deficient olefins. The inventive processes may be performed with or without a solvent. Solvents that have shown promising results include chloroform (deuterated) and anhydrous polyether of glycol. By the processes of the present invention using solvents yields greater than 40%, desirably 50% and more desirably 75% may be achieved. Where a solvent is not used, yields in the vicinity of 30% have been achieved.

In any of these aspects, the process may be conducted with or without added catalyst, as noted above.

Reference to FIG. 1 may be useful to appreciate further the present invention, which is described in more detail below and in the Examples section that follows.

Thus, as an initial reactant in the inventive processes are aldehyde compounds having the structure R—CH═O, where R is hydrogen or vinyl. The aldehyde compound may be an aldehyde itself or a source of an aldehyde, such as one that yields an aldehyde like formaldehyde under reaction conditions. The aldehyde compound in a desirable embodiment includes formaldehyde (or a source thereof, such as paraformaldehyde), formalin, 1,3,5-trioxane, or vinyl aldehydes, such as acrolein.

As a reactant with such an aldehyde is a primary amine, such as aniline, N-methylamine, N-propylamine or tertiary butylamine. Desirably, the primary amine is tertiary butylamine.

An imine is formed from the reaction of the aldehyde compound and the primary amine. (See FIG. 1, A.)

Examples of imines formed therefrom thus include N-methylidene-tertiary butylamine, N-methylideneaniline, N-methylidenemethylamine and N-methylidenepropylamine. For instance, see J. March, Advanced Organic Chemistry, Third Edition, Wiley & Sons Inc., 417 (1985), and references cited therein.

The so-formed imines may be converted into iminium salts by contacting them with an acidic species, such as trifluoroacetic acid, acetic acid, sulfuric acid, methane sulfonic acid and camphor sulfonic acid [see e.g. March at 802, and references cited therein; see also M. B. Smith, Organic Synthesis, McGraw Hill international, Chemistry Series, 1302 (1994) and references cited therein and Abbaspour Tehrani and De Kimpe, *Science of Synthesis*, 27, 313 (2004), and references cited therein]. Desirably a mixture of acids may be used, such as sulfuric acid in combination with methane sulfonic acid. (See FIG. 1, B.)

The iminium salt may be represented as follows:

$$\begin{matrix} R_1 \\ \diagdown \\ \diagup \\ R_2 \end{matrix} = \overset{+}{N} \begin{matrix} R_3 \\ \diagup \\ \diagdown \\ R_4 \end{matrix} \quad X^-$$

where $R_1$, $R_2$, $R_3$ are each H and $R_4$ is an alkyl, such as tertiary butyl; $X^-$ is $SO_3CH_3^-$, for example, or $0.5(SO_4^{2-})$, or $HSO_4^-$, or mixtures of such anions if a mixture of the corresponding acids has been used during protonation of the imine.

Some non-protonated iminium salts are available commercially, such as Eschenmoser's salt, which is available from The Aldrich Chemical Co. Eschenmoser's salt has been used in the synthesis of conventional acrylates, see e.g. Hin, B., Majer, P., Tsukamoto, T., *J. Org. Chem.*, 67, 7365 (2002).

This iminium salt has also been used in Mannich reactions [Holy et al, *Tetrahedron,* 35, 613 (1979), and Bryson et al, *J. Org. Chem.,* 45, 524 (1980)]. As will be seen in the Examples, such a non-protonated iminium salt does not provide satisfactory results.

The iminium salts are then reacted with compounds containing a methylene linkage having at least one electron withdrawing substituent attached thereto. In these compounds, the electron withdrawing substituent is selected from nitrile, carboxylic acids, carboxylic esters, sulphonic acids, ketones or nitro. In a desirable embodiment, these compounds have two or more electron withdrawing substituents, which may be the same or different, such as a nitrile group and an ester group—in this case, a cyanoacetate. (See FIG. 1, C.)

Representative examples of these compounds include malononitrile, malonic acid and its esters, ethyl nitroacetate, cyanoacetate esters, 4-cyclopentene-1,3-dione, cyclopentane-1,3-dione, 4-cyclohexene-1,3-dione, cyclohexane-1,3-dione, 2,2-dimethyl-1,3-dioxane-4,6-dione (Meldrum's acid), and tetronic acid, some of which are commercially available for instance from Aldrich Chemical Co. A particularly desirable example is a cyanoacetate.

The structures below illustrate the olefinic products—conjugated or not—that would result from a reaction involving iminium salts with paraformaldehyde, formalin and/or acrolein using the above reactants.

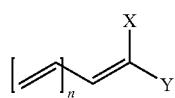

I

Here, when a source of formaldehyde is used, n is 0 in structure I and a methylenic compound results with X and Y being nitrile, carboxylic acid, or carboxylic acid esters; X being nitro and Y being carboxylic acid ester; or X being nitrile and Y being carboxylic acid ester, the latter combination giving rise to 2-cyanoacrylates using alkyl cyanoacetates as a substrate, for example. When acrolein is used, n is 1 and the same combinations of X and Y can apply in structure I.

The electron deficient olefin so formed by the inventive processes may be a variety of olefins having at least one electron withdrawing group attached thereto. In a desirable embodiment, as noted above with respect to the second reactant, the reactive electron deficient olefin so formed will have two or more electron withdrawing groups attached thereto, which may be the same or different. Particularly desirable products have two electron withdrawing groups attached thereto which are different, such as 2-cyanoacrylate esters.

Representative examples of 2-cyanoacrylate esters so formed by the inventive processes include methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethyl siloxane esters of 2-cyanoacrylic acid.

Of course, salt—an ammonium salt—is also formed (See FIG. 1, C.)

The reaction of the inventive processes proceed sin solvent either forming a solution or a suspension. Chloroform (such as deuterated chloroform) has been used. In addition, different solvents may be used, such as chlorobenzene, tetrachloroethene, toluene, THF, 1,4-dioxane, (poly)ethylene glycol dialkyl ethers or esters. The reaction of the inventive processes may proceed with or without heating or cooling, depending of course on the specific reactants and the scale of the reaction.

Decomposition of the source of formaldehyde, e.g., paraformaldehyde, may occur under gentle heating up to a temperature of 70° C., to liberate formaldehyde in situ in the reaction medium. The temperature may be reached through an external heating element or internally by means of the exotherm that may be generated depending on the identity of the reactants. The temperature of the reaction should be controlled however to accommodate any such exothermic processes.

The time of reaction may be monitored by reference to the formation of the desired electron deficient olefin product. $^1$H NMR spectrometer is a particularly useful tool in this regard. The time of reaction may be as little as 30 minutes, for instance, or longer or shorter for that matter depending again on the identity of the specific reactants, the scale of the reaction and whether heat is added to the reaction conditions.

Once formed, the electron deficient olefin may be isolated as a product by removing solvent and then subsequently distilling under vacuum or by freezing it in a solid form and separating off the liquid phase.

The electron deficient olefin so formed by the inventive processes may be stabilized during the synthesis and/or isolation procedure, and also in the isolated product to improve its shelf life. Suitable stabilizers include free radical stabilizers and acidic stabilizers, particularly in the case of 2-cyanoacrylate esters formed as the product of such inventive processes.

For example, free radical stabilizers include hydroquinone, pyrocatechol, resorcinol or derivatives thereof, such as hydroquinone monoethyl ether, or phenols, such as di-t-butylphenol or 2,6-di-t-butyl-p-cresol, 2,2'-methylene-bis-(4-methyl-6-t-butylphenol), bisphenol A, dihydroxydiphenylmethane, and styrenized phenols.

For example, acidic stabilizers include Lewis acids, sulfuric acid, hydrochloric acid, sulfonic acids, such as methane, ethane or higher sulfonic acids, p-toluene sulfonic acid, phosphoric acid or polyphosphoric acids, silyl esters of strong acids, such as those derived from trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The amount of either stabilizer used to stabilize the electron deficient olefin prepared by the inventive processes is well known to those of ordinary skill in the art, and may be varied depending on the properties of the resulting composition made from the so formed electron deficient olefin.

The following example is intended to illustrate but in no way limit the present invention.

Example

Imine Formation

N-Methylidenemethylamine was prepared by mixing paraformaldehyde and an aqueous solution of methylamine (40%) with stirring at room temperature for a period of time of 2 hours. The reaction product was extracted with dichloromethane and dried. The reaction product was identified by $^1$H NMR to be a cyclic trimer.

N-Methylidenebutylamine was prepared by adding tertiary butylamine (1 eq) directly and portionwise to paraformaldehyde (1 eq) over a period of time of 30 minutes, with stirring and cooling to maintain the temperature close to room temperature. After addition, stirring was continued for a further period of time of 30 minutes at room temperature. Stirring was discontinued and the mixture separated into a pale light oily organic layer and an aqueous layer. The organic layer was separated, dried, and then purified by distillation.

N-Methylidenepropylamine was prepared following the same procedure previously described in B above, replacing tertiary butylamine with propylamine.

N-Methylideneaniline was prepared by mixing paraformaldehyde and aniline in chloroform at room temperature for a period of time of 2 hours and then heating at a temperature of 50° C. for a period of time of 3 hours.

The imines formed above were characterised by $^1$H NMR and FTIR.

Iminium Salt Formation

In a glass tube, N-methylidenebutylamine from above (0.43 g, 5 mmol) was dissolved in deuterated chloroform (2 ml) under stirring and cooling to a temperature of 0° C. under anhydrous conditions. A mixture of acids—the combination of methane sulfonic acid and sulfuric acid—was added slowly to give an excess of acid and ensure conversion of imine to iminium salt. The reaction was observed to be exothermic.

Reaction of Iminium Salt with Methylene Compounds Bearing Electron Withdrawing Groups Ethyl cyanoacetate (0.57 g, 0.53 mL, 5 mmol) was added directly to the solution of iminium salt described above, at room temperature with stirring. The reaction mixture was further stirred and heated to a temperature of 70° C. A 60% yield of ethyl-2-cyanoacrylate monomer was observed to have resulted after a period of time of 1 hour and a 64% yield after a period of time of 3 hours at that temperature as measured by internal referencing using $^1$H NMR conducted directly on the reaction solution.

Significantly, no oligomer or polymer was observed to have formed by $^1$H NMR analysis, which is surprising because the so-formed monomer is reactive under conventional base-catalyzed Knoevenagel conditions the monomer polymerizes and which must subsequently cracked to yield the monomer. Furthermore, $^1$H NMR showed that some unreacted ethyl cyanoacetate remained in solution ready for further conversion directly to monomer.

After removal of solvent, the glassware (previously acid washed) was reconfigured for vacuum distillation and one drop of methane sulfonic acid was placed in receiver flasks. Only ethyl cyanoacetate and ethyl-2-cyanoacrylate monomer distilled over and were collected in the liquid state. No polymer was observed to have formed at any time during the operation.

Reaction of Eschenmoser's Salt with Methylene Compounds Bearing Electron Withdrawing Groups For comparative purposes, Eschenmoser's iodide salt—a non-protonated iminium salt—was employed as a commercially available iminium salt, and was placed in deuterated chloroform and observed to be scarcely soluble. When MeSO$_3$H and H$_2$SO$_4$ were added the solubility was observed to increase. After heating in the presence of ethyl cyanoacetate on an equimolar basis at a temperature of 70° C. for a period of time of 3 hours, the reaction produced monomeric cyanoacrylate in low yield.

Iminium Salt Formation

In a round bottom flask, N-methylidenebutylamine from above (0.43 g, 5 mmol) was dissolved in diethylene glycol dibutyl ether (2 ml) (99+% from Aldrich), previously dried, under stirring and cooling to a temperature of 10° C. under anhydrous conditions. Methane sulfonic acid was added slowly to give an excess of acid and ensure conversion of imine to iminium salt. The reaction was observed to be exothermic.

Reaction of Iminium Salt with Methylene Compounds Bearing Electron Withdrawing Groups Ethyl cyanoacetate (0.57 g, 0.53 mL, 5 mmol) was added directly to the solution of iminium salt described above in paragraph [0062], at room temperature with stirring. The reaction mixture was further stirred and heated to a temperature of 85° C. A 50% yield of ethyl-2-cyanoacrylate monomer was observed to have resulted after a period of time of 1 hour as measured by internal referencing using $^1$H NMR diluting a sample of the reaction solution in CDCl$_3$.

Significantly, no oligomer or polymer was observed to have formed by $^1$H NMR analysis, which is surprising because the so-formed monomer is reactive under conventional base-catalyzed Knoevenagel conditions the monomer polymerizes and which must subsequently cracked to yield the monomer. Furthermore, $^1$H NMR showed that some unreacted ethyl cyanoacetate remained in solution ready for further conversion directly to monomer.

Reaction of Iminium Salt with Methylene Compounds Bearing Electron Withdrawing Groups with the Solvent Removed Ethyl cyanoacetate (0.53 ml, 5 mmol) was added directly to the solution of iminium salt described above, at room temperature with stirring and the solvent was removed under vacuum. The reaction mixture was further stirred and heated to a temperature of 70° C. About 30% yield of ethyl-2-cyanoacrylate monomer was observed to have resulted after a period of time of 15 minutes as measured by internal referencing using $^1$H NMR conducted diluting the reaction crude in CDCl$_3$.

What is claimed is:

1. A process for the preparation of a reactive electron deficient olefin, steps of which comprise
    (a) providing as reactants an aldehyde compound having the structure R—CH=O, wherein R is hydrogen or vinyl and a primary amine to form an imine;
    (b) contacting the imine formed in step (a) with acid to form an iminium salt;
    (c) providing a 2-electron withdrawing group-substituted methylene compound and reacting the iminium salt from step (b) therewith to form an electron deficient olefin; and
    (d) optionally, separating from step (c) the so formed reactive electron deficient olefin to yield the reactive electron deficient olefin substantially free from reactants and solvent.

2. A process for the preparation of a 2-cyanoacrylate ester, steps of which comprise
    (a) providing as reactants an aldehyde compound or a source of an aldehyde compound, and a primary amine;
    (b) reacting the mixture of reactants under appropriate conditions and for a time sufficient to yield an imine;
    (c) contacting the imine formed in step (b) with acid to form an iminium salt;
    (d) providing a cyanoacetate and reacting the iminium salt from step (c) therewith to form 2-cyanoacrylate ester; and
    (e) separating from the mixture the so-formed 2-cyanoacrylate ester to yield 2-cyanoacrylate ester substantially free from reactants and solvent.

3. A process for the preparation of a reactive electron deficient olefin, steps of which comprise (a) providing an iminium salt and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;

(b) reacting the iminium salt and the compound under appropriate conditions and for a time sufficient to yield a reactive electron deficient olefin; and (c) optionally, separating from the mixture the so formed reactive electron deficient olefin to yield the reactive electron deficient olefin substantially free from the iminium salt, the solvent and the compound, wherein the process is conducted without any added catalyst.

4. The process of claim 1, wherein the compound containing a methylene linkage having at least one electron withdrawing substituent attached thereto is an ester of cyanoacetic acid.

5. The process of claim 1, wherein the aldehyde compound is a member selected from the group consisting of paraformaldehyde, formalin, 1,3,5-trioxan and acrolein.

6. A process for the preparation of a reactive electron deficient olefin, steps of which comprise (a) providing an iminium salt and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;

(b) reacting the iminium salt and the compound under appropriate conditions and for a time sufficient to yield a reactive electron deficient olefin; and (c) optionally, separating from the mixture the so formed reactive electron deficient olefin to yield the reactive electron deficient olefin substantially free from the iminium salt, the solvent and the compound, wherein the electron deficient olefin is a biscyanoacrylate, biscyanopentadienoate or a bis-alkylene derived from dimalonates or malononitrile.

7. A process for the preparation of a reactive electron deficient olefin, steps of which comprise (a) providing an iminium salt and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;

(b) reacting the iminium salt and the compound under appropriate conditions and for a time sufficient to yield a reactive electron deficient olefin; and (c) optionally, separating from the mixture the so formed reactive electron deficient olefin to yield the reactive electron deficient olefin substantially free from the iminium salt, the solvent and the compound, wherein the electron deficient olefin is a compound having one end terminating with a cyanoacrylate, cyanopentadienoate, or alkylene derived from dimalonate and another end terminating with a group selected from the group consisting of branched and unbranched alkyl esters, esters containing aromatics and hetrocylic nuclei, acrylates, cyanoacrylates, siloxanes, blocked and unblocked isocyanates, anhydrides, silanes, vinyls, acetylenes, and epoxies.

8. The process of claim 1, wherein the electron deficient olefin is a 2-cyanoacrylate.

9. The process of claim 8, wherein the 2-cyanoacrylate is selected from the group consisting of methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethylsiloxane esters of 2-cyanoacrylic acid.

10. The process of claim 1, wherein the acid is the combination of methane sulfonic acid and sulfuric acid.

11. A process for the preparation of a reactive electron deficient olefin, steps of which comprise (a) providing an iminium salt and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;

(b) reacting the iminium salt and the compound under appropriate conditions and for a time sufficient to yield a reactive electron deficient olefin; and (c) optionally, separating from the mixture the so formed reactive electron deficient olefin to yield the reactive electron deficient olefin substantially free from the iminium salt, the solvent and the compound, wherein the yield of the reactive electron deficient olefin is greater than 40%.

12. The process of claim 2, wherein the yield of the 2-cyanoacrylate ester is greater than 40%.

13. The process of claim 2, wherein the acid is the combination of methane sulfonic acid and sulfuric acid.

14. The process of claim 1, wherein the yield of the reactive electron deficient olefin is greater than 40%.

15. The process of claim 1, wherein the iminium salt is provided in a solvent to form a solution.

16. The process of claim 1, wherein the imine is contacted with acid in a solvent.

17. The process of claim 2, wherein the imine is contacted with acid in a solvent.

18. The process of claim 7, wherein the iminium salt is provided in a solvent to form a solution.

* * * * *